United States Patent
Schiavinato et al.

(10) Patent No.: US 12,251,416 B2
(45) Date of Patent: Mar. 18, 2025

(54) PHARMACEUTICAL COMPOSITIONS CONTAINING HYALURONIC ACID AND CARNOSINE AND RELATIVE USE

(71) Applicant: FIDIA FARMACEUTICI S.P.A., Abano Terme (IT)

(72) Inventors: Antonella Schiavinato, Abano Terme (IT); Valentina Greco, Abano Terme (IT); Luciano Messina, Abano Terme (IT); Susanna Vaccaro, Abano Terme (IT); Enrico Rizzarelli, Catania (IT); Sebastiano Sciuto, Pedara (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 0 days.

(21) Appl. No.: 17/482,696

(22) Filed: Sep. 23, 2021

(65) Prior Publication Data

US 2022/0031797 A1    Feb. 3, 2022

Related U.S. Application Data

(63) Continuation of application No. 16/753,152, filed as application No. PCT/IB2018/057697 on Oct. 3, 2018, now abandoned.

(30) Foreign Application Priority Data

Oct. 3, 2017 (IT) .......................... 102017000110784

(51) Int. Cl.
| | |
|---|---|
| *A61K 38/05* | (2006.01) |
| *A61K 31/728* | (2006.01) |
| *A61K 47/61* | (2017.01) |
| *A61K 47/64* | (2017.01) |
| *A61P 19/02* | (2006.01) |
| *A61P 19/10* | (2006.01) |
| *A61P 29/00* | (2006.01) |
| *A61K 9/00* | (2006.01) |

(52) U.S. Cl.
CPC ............ *A61K 38/05* (2013.01); *A61K 31/728* (2013.01); *A61K 47/64* (2017.08); *A61P 19/02* (2018.01); *A61P 19/10* (2018.01); *A61K 9/0014* (2013.01); *A61K 9/0029* (2013.01); *A61K 9/0053* (2013.01)

(58) Field of Classification Search
CPC ........ A61K 38/05; A61K 47/61; A61K 47/64; A61K 9/0014; A61K 9/0029; A61K 9/0053; A61K 31/728; A61K 47/542; A61P 19/02; A61P 19/10; A61P 29/00
See application file for complete search history.

(56) References Cited

U.S. PATENT DOCUMENTS

| | | | |
|---|---|---|---|
| 7,708,994 B2* | 5/2010 | Benyunes | ............... A61P 19/02 424/143.1 |
| 2014/0161855 A1 | 6/2014 | Doucet et al. | |
| 2014/0248249 A1* | 9/2014 | Patel | ..................... A61K 9/0014 514/474 |
| 2017/0246306 A1 | 8/2017 | Sciuto et al. | |

FOREIGN PATENT DOCUMENTS

| | | |
|---|---|---|
| EP | 1 176 154 A1 | 1/2002 |
| EP | 1 724 287 A1 | 11/2006 |
| EP | 1 853 279 A1 | 11/2007 |
| EP | 1 860 116 A1 | 11/2007 |
| WO | WO 2005/082433 A1 | 9/2005 |
| WO | WO 2006/092233 A1 | 9/2006 |
| WO | WO 2012/076961 A2 | 6/2012 |
| WO | WO 2016/016847 A1 | 2/2016 |

OTHER PUBLICATIONS

Sodium Hyaluronate vs. Hyaluronic Acid: What's the Difference? from Pharmagel, https://pharmagel.net/pages/sodium-hyaluronate-vs-hyaluronic-acid-what-s-the-difference, pp. 1-5. Accessed May 19, 2023. (Year: 2023).*
Campo et al. "Hyaluronan reduces inflammation in experimental arthritis by modulating TLR-2 and TLR-4 cartilage expression", Biochimica Et Biophysica Acta, 2011, vol. 1812, pp. 1170-1181.
Definition of derivative from dictionary.com, pp. 1-7. (Year: 2011).
Dráfi et al. "Carnosine inhibits degradation of hyaluronan induced by free radical processes in vitro and improves the redox imbalance in adjuvant arthritis in vivo", Neuroendocrinology Letters, Dec. 28, 2010, vol. 31, Suppl . 2, pp. 96-100.
International Search Report, issued in PCT/IB2018/057697, dated Jan. 24, 2019.
Written Opinion of the International Searching Authority, issued in PCT/IB2018/057697, dated Jan. 24, 2019.

* cited by examiner

*Primary Examiner* — Julie Ha
(74) *Attorney, Agent, or Firm* — Birch, Stewart, Kolasch & Birch, LLP

(57) ABSTRACT

Pharmaceutical compositions are described containing Hyaluronic Acid and Carnosine for use in the treatment and prevention of osteoarthritis (OA) and for the treatment of rheumatoid arthritis (RA).

10 Claims, 4 Drawing Sheets

PHARMACEUTICAL COMPOSITIONS CONTAINING HYALURONIC ACID AND CARNOSINE AND RELATIVE USE

CROSS-REFERENCE TO RELATED APPLICATIONS

This application is a Continuation of application Ser. No. 16/753,152, filed on Apr. 2, 2020, which is the National Phase under 35 U.S.C. § 371 of International Application No. PCT/IB2018/057697, filed on Oct. 3, 2018, which claims the benefit under 35 U.S.C. § 119(a) to Patent Application No. 102017000110784, filed in Italy on Oct. 3, 2017, all of which are hereby expressly incorporated by reference into the present application.

The present invention relates to pharmaceutical compositions containing Hyaluronic Acid and Carnosine and their relative use.

FIELD OF THE INVENTION

Osteoarthritis (OA) is a severely disabling pathology characterized by the progressive erosion of articular cartilages due to degradation of the matrix and the loss of the main cartilaginous cellular components: chondrocytes.

The etiology is still partly unknown, recent experimental results, however, have shown that the mechanical imbalance that can involve the joint in its complexity may also be the initial cause of the onset of the above-mentioned pathology.

Excessive and/or incorrect loading of the joints can in fact cause a chondrocyte response that is expressed in the synthesis of those enzymes responsible for the degradation of the cartilage itself. These protease enzymes are called Metalloprotease (MMP) and are synthesized by chondrocytes when stimulated by pro-inflammatory cytokines, such as IL-1, IL-6 and TNT-α, which are produced and released in the joint cavity above all due to the onset of an inflammatory pathology. These cytokines also stimulate the synthesis of high levels of nitric oxide (responsible for death by apoptosis of chondrocytes) and, moreover, inhibit the synthesis of proteoglycans (structural components of the matrix) (Dozin B. et al., Matrix Biology, 2002, 21:449-459).

High levels of pro-inflammatory molecules have also been found in the synovial fluid of patients suffering from rheumatoid arthritis (RA) and psoriatic arthritis (Arend W. P. et al., Arthritis Rheum, 1995, 38:151-160).

Rheumatoid arthritis (RA) is a chronic, ankylosing and progressive inflammatory polyarthritis with autoimmune pathogenesis and unknown etiology, mainly due to the synovial joints in which it causes deformation and pain until the loss of joint functioning. The progression of RA, in fact, determines a strong inflammatory response of the synovium with a consequent swelling of its cells, an excess of synovial fluid and the development of fibrous tissue. More specifically, the synovium is a membrane of mesenchymal origin formed by synoviocytes (of the macrophage and fibrinoidal type) which, in the disease, undergoes hyperplasia and hypertrophy and then grows in thickness (the two/three layers of a non-pathological condition become seven or more), forming the synovial pannus that begins to peripherally erode the bone not covered by cartilage.

At the same time, the polymorphonuclear cells with T, B lymphocytes and plasma cells move into the synovial fluid, increasing the inflammation of the affected joint, the articular cartilage affected by RA (with relative underlying bone) then undergoes thinning with progressive destruction.

This pathology generally manifests itself at a systemic level also involving other organs and apparatuses. Rheumatoid nodules are typical, that can be formed at the pulmonary level with consequent pulmonary fibrosis, pleurisy and pleuropericarditis, at the cardiac level there can be an acceleration of coronary atherosclerosis, whereas at an ocular level there can be xerophthalmia, uveitis and scleritis. Amyloidosis and osteoporosis are also complications of RA (Cecil, TEXTBOOK of MEDICINE, 1988).

Rheumatoid arthritis affects from 0.5 to 1% of adults in the world, and commonly begins between the age of 40 and 50 years.

The treatment of RA is difficult, it depends on its severity and the type of organs involved and includes the use of drugs suitable for controlling inflammation for the prevention and/or treatment of joint damage (in addition to other organs) with the aim of slowing down the resulting disability. Pain-relieving and anti-inflammatory drugs, including steroids and NSAIDs, suppress the symptoms but do not stop the progression of the condition, anti-rheumatic drugs modifying the disease (DMARD) can, however, slow it down.

In more aggressive forms, methotrexate is generally used, an antimetabolite inhibitor of the synthesis of folic acid which, at low doses, acts as an immunosuppressant, but recently biological drugs have been introduced that act in a more selective and specific way (Canete J D et al. Expert Opinion Biol Ther, 2017, 17:1-15), such as Etanercept, a fusion protein that acts by antagonizing the pro-inflammatory cytokine.

TNF is part of that group of cytokines responsible for the acute phase of systemic inflammation; it is involved in numerous processes such as cell proliferation, differentiation and apoptosis, carcinogenesis and viral replication. It is mostly produced by macrophages; its synthesis can be stimulated by bacterial endotoxins and be inhibited by steroids.

Acting on numerous organs and systems, together with other cytokines, it promotes the inflammatory response which in turn ignites many pathologies (including autoimmune diseases) such as RA and OA, Crohn's disease, psoriasis and asthma; this cytokine is also capable of activating osteoclasts and therefore inducing bone resorption, it is capable of stimulating the macrophage production of molecules with an oxidizing action, it is involved in particular pathologies of the cardiovascular system participating in the formation of venous thrombi, in the pathogenesis of atherosclerosis and vasculitis (Alam J., Biomed Pharmacother, 2017, 92:615-633), and finally it is capable of increasing the resistance of tissues to insulin favouring the onset of type II diabetes (Nicolau J et al., Joint Bone Spine 2017, 84 (4):411-416).

For OA and RA there are various types of drugs which are effective in slowing down the progression of the above-mentioned pathologies or in the treatment of related symptoms, however they can have important side-effects, often toxic, both as synthetic molecules (therefore not natural), for the pharmacological treatment regimen that must be sustained for very long periods of time, and also for the method of administration, generally parenteral, but above all oral and therefore involving the whole organism even if, in many cases, only the inflamed joint is to be treated.

The objective of the present invention is therefore to identify pharmaceutical compositions comprising hyaluronic acid (HA)/carnosine conjugate particularly effective for use in the treatment and prevention of OA and in the treatment of RA (with all the consequent diseases caused directly by RA or indirectly related to/depending on RA), preferably by oral administration (above all when the disease has acquired clear systemic manifestations) and/or by intra-articular administration in the joint in an early stage of the disease, or in an intensification localized phase in the same joint.

Carnosine is a dipeptide obtained from the condensation reaction between β-alanine and L-histidine, in the body. It is found in large quantities in the muscles and in the brain; scientific literature is unanimous in giving it an anti-oxidant, anti-radical and anti-inflammatory activity (Budzen S. et al., Adv Clin Exp Med, 2013, 22 (5): 739-44).

Pre-clinical studies have demonstrated its anti-radical capacity in the prevention and treatment of cataracts (Babizhayev M. et al., Biophys, Acta, 1989, 1004 (3):363-371), whereas its anti-inflammatory activity has been demonstrated in some tissues of the digestive system, in the eyes and in the skin (U.S. Pat. No. 4,508,728, WO01/52808); its specific activity as a scavenger against radical hydroxyl has also been demonstrated (La Mendola D. et al., Helv. Chim. Acta, 2002, 85 (6):1633-1643).

The peptide nature of carnosine, however, imposes some limitations on its use, limitations associated with its thermolabile nature and its high in vivo degradability due to specific peptidases. In order to overcome this limitation, the use of N-acetyl-carnosine (WO95/10294) has been proposed, which is degraded much more slowly than the free version (Babizhayev M A et al., Clin. Chim. Acta, 1996, 254 (1):1-21) and, at the same time, the chemical derivative of carnosine has also been synthesized with cyclodextrins (EP1176154), natural cyclic oligosaccharides used in medicine as drug carriers. In this case, the cyclodextrin stabilizes the dipeptide, protecting it from the hydrolytic activity of carnosinase (Schaschke N. et al., JACS 1998, 120 (28): 7030-7038), thus allowing the above-mentioned molecule to exert its biological activity. Based on the same rationale, the carnosine conjugate with trehalose was subsequently patented as a system with an anti-oxidant, anti-glycating and anti-aggregating activity (EP1860116).

The derivative of HA is also known, which is obtained by conjugating carnosine with said polysaccharide by an amide bond involving the carboxyl of HA and the amino group of the dipeptide (WO2016016847).

Use in the treatment of RA and OA, however, was not contemplated for this derivative; furthermore, according to the above-mentioned reference, this derivative could only be derivatized up to 25% (mole/mole ratio between HA and carnosine).

The present invention describes a composition comprising the amide derivative of HA with carnosine with a degree of derivatization higher than 25%, therefore a conjugate whose synthesis was not considered possible by skilled persons in the field based on the teaching of the state of the art.

HA is a hetero-polysaccharide composed of alternating residues of D-glucuronic acid and N-acetyl-D-glucosamine. It is a linear chain polymer with a molecular weight ranging from 50,000 to 13×106 Da, depending on the source from which it is obtained and the preparation methods used. It is present in nature in pericellular gels, in the fundamental substance of the connective tissue of vertebrate organisms, in the synovial fluid of the joints, in the vitreous humor and in the umbilical cord. HA therefore plays an important role in the biological organism, both as a mechanical support of the cells of many tissues such as the skin, tendons, muscles and cartilage, and also as an active agent capable of modulating (through the CD44 receptor) many processes relating to cell physiology and biology, such as, for example, proliferation, migration, cell differentiation and angiogenesis; its role in maintaining the hydration of the tissues and lubrication of the joints is also known. HA is in fact a polysaccharide that has particular viscoelastic properties, synthesized and secreted in the joint cavity mainly by synoviocytes (Asari A. et al., Arch. Histol. Cytol., 1995, 58 (1):65-76) and it is one of the main components of the synovial fluid. During slow movements of the joint, HA acts as a viscous lubricant, whereas during fast movements, it absorbs with elastic properties any possible traumas or microtraumas that may strike the joint.

The exchange of HA in the non-pathological synovial fluid is generally extremely fast, whereas in OA a decrease in concentration has been found with a lowering of the average molecular weight (MW), but above all a sharp decrease in its exchange flow (Balazs E A, et al., J Rheumatol, Suppl., 1993, 12: 75-82).

For these reasons, Balazs first suggested the possibility of modifying the evolution of the osteoarthritic process through the contribution of exogenous HA (especially with a high MW) directly in the joint cavity, and thanks to this treatment therapy it was possible to demonstrate the protective effect of HA against the degeneration involved in the cartilage of a joint damaged by inflammatory diseases or trauma.

DETAILED DESCRIPTION

Figure 1:
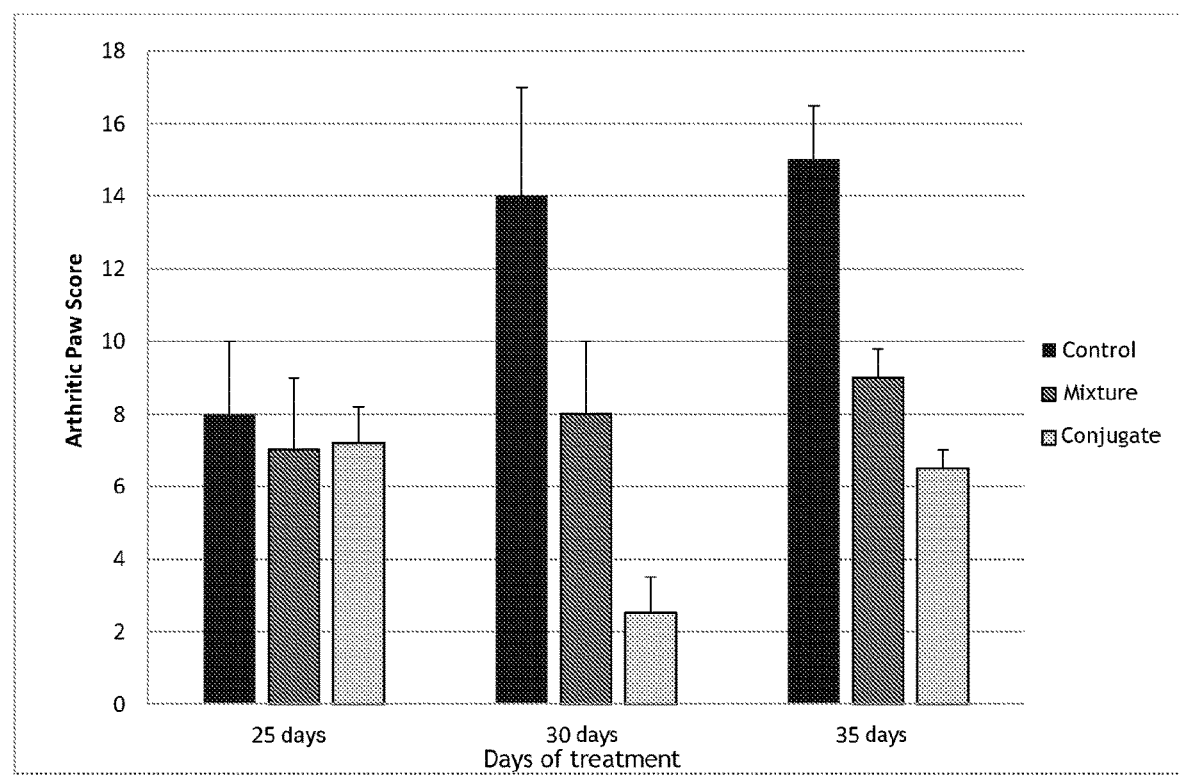
FIG. 1 shows the maximum index of pathological manifestation with the Arthritic Paw Score.

The object of the present invention relates to a pharmaceutical composition comprising a hyaluronic acid (HA)/carnosine conjugate with a direct amide bond between the carboxyl group of HA and the amino group of carnosine for use in the prevention and treatment of OA, in the treatment of RA and pathologies caused directly by RA or indirectly related to/depending on RA, in particular for use in the treatment of diseases caused directly by RA selected from the group comprising pulmonary fibrosis, pleurisy and pleuropycarditis, xerophthalmia, uveitis and scleritis, or indirectly related to/depending on RA selected from the group including premature pathological aging, heart attack, stroke, arterosclerosis and coronary atherosclerosis, arterial hypertension, dementia, diabetes, osteoporosis and amyloidosis, cancer, proteinuria and nephritis, gastric lesions, cataracts, psoriatic arthritis, gastritis, vasculitis, type I diabetes and autoimmune thyroiditis. This use will lead to an undoubted therapeutic benefit as a direct consequence of the treatment of RA from which these diseases derive.

The pharmaceutical compositions for use according to the present invention preferably comprise the HA/carnosine conjugate with a degree of derivatization (amidation) of the carboxyl group of HA (DS) higher than 25% (from 25% to 100%), preferably ranging from 30% to 100%, more preferably ranging from 30% to 60%, and even more preferably varying within the range of 35±3% (i.e. from 32% to 38%) to 45±5% (i.e. from 40% to 50%).

Said amide derivative of HA with carnosine (ie HA/carnosine conjugate) is obtained by covalently combining the dipeptide (i.e. carnosine) with hyaluronic acid (HA) by forming a direct amide bond (without the aid of permanent spacers) between carboxyl of HA and amine group of carnosine.

As demonstrated hereunder, the Applicant has in fact surprisingly discovered how the conjugate object of the invention, has unexpected synergistic effects between carnosine and HA in the curative treatment of RA and OA, achieving a significant clinical/histological improvement of the above-mentioned pathologies, with a significant reduction in plasma indicators of both inflammation and lipid oxidation.

The degree of derivatization of the conjugate object of the present invention is measured by the method described in the following Example 4.

The HA used for the synthesis of the HA/carnosine conjugate of the present invention can derive from any source, for example, by extraction from rooster combs (EP138572), by fermentation (from *Streptocuccus equi* or *Zooepidemicus*, EP716688), or by biosynthesis (from *Bacillus*, EP2614087), and can have an average molecular weight (MW) ranging from 400 to 3×106 Da, in particular from $1 \times 10^5$ Da to $1 \times 10^6$ Da, even more particularly within the range of 130-220 kDa and/or within the range of 500-750 kDa.

Pharmaceutical compositions are preferred wherein the degree of derivatization of HA varies within the range of 30 to 60% and the average molecular weight of HA ranges from $1 \times 10^5$ Da to $1 \times 10^6$ Da; pharmaceutical compositions wherein the DS of HA varies within the range of 30 to 60% and the average molecular weight of HA is within the range of 130-220 k Da, or 500-750 k Da and relative mixtures, are more preferred.

Even more preferred are pharmaceutical compositions wherein the DS of HA varies within the range of 31 to 34% (3S±3%) or within the range of 40 to 50% (45±5%) and relative mixtures, and the average molecular weight of HA is within the range of 130-220 kDa or 500-750 kDa and relative mixtures; in particular, pharmaceutical compositions are preferred wherein, when the DS of HA varies within the range of 35±3%, the average molecular weight of HA is within the range of 500-750 kDa, and when the DS of HA varies within the range of 45±5%, the average molecular weight of HA is within the range of 130-220 kDa.

It should be pointed out that average molecular weight refers to the weight average MW calculated with the "intrinsic viscosity" method (Terbojevich et al., Carbohydr Res, 1986, 363-377).

The hyaluronic acid used for the synthesis of the conjugate in question is selected from the sodium salt of HA (EP138572), preferable for the synthesis of the HA/carnosine conjugate up to a DS of about 40% (therefore from 25% to 40%), and the tetrabutylammonium (TBA) salt of HA (EP216453), preferable for the synthesis of the HA/carnosine conjugate with a DS higher than 40% (therefore from 40% to 100%), the final product (described in the preparation examples provided hereunder) being (preferably) prepared as the sodium salt of the HA/carnosine conjugate, regardless of the HA salt used as reagent.

A further object of the invention relates to biomaterials consisting of conjugated HA derivatives (again through the amide bond) with carnosine, in the modes and in the degrees described for HA, defined herein as "HA/carnosine biomaterials".

The HA derivatives that can be used in the formation of the above-mentioned biomaterials are listed hereunder:

HYAFF®: esters of HA with alcohols of the aliphatic, araliphatic, cycloaliphatic, aromatic, cyclic and heterocyclic series, with an esterification percentage that can vary depending on the type and length of the alcohol used, preferably from 1 to 70%, whereas the remaining percentage of non-esterified HA can be salified with organic and/or inorganic bases (EP216453);

HYADD®: amides of HA with amines of the aliphatic, araliphatic, cycloaliphatic, aromatic, cyclic, and heterocyclic series, with an amidation percentage ranging from 0.1 to 50%, whereas the remaining percentage of HA not subjected to amidation can be salified with organic and/or inorganic bases (EP1095064);

ACP®: internal esters of HA with an esterification percentage not higher than 20%, preferably ranging from 0.05 to 10% of esterification, whereas the remaining percentage of non-esterified HA can be salified with organic and/or inorganic bases (EP341745);

HYOXX®: derivatives of percarboxylates of HA obtained by the oxidation of the primary hydroxyl of the N-acetyl-glucosamine fraction with a percarboxylation degree ranging from 0.1 to 100% and, preferably, from 25 to 75%. The carboxyl groups of HA can be salified with organic and/or inorganic bases (EP1339753).

O-sulfated derivatives of HA up to the 4th degree of sulfation (EP702699).

It is also possible to start from the HA/carnosine conjugate to synthesize (according to what is known to skilled persons in the field) the above-mentioned HA/carnosine biomaterials further derivatizing the HA: it is therefore possible to use the conjugate in question as starting material (instead of the HA sodium salt or TBA salt) to proceed with the synthesis of HYAFF, ACP, HYADD, HYOXX or sulfated derivatives according to what is known to skilled persons in the field, to obtain products previously defined as HA/carnosine biomaterials.

Esters and amides are, among the derivatives of HA, those that are particularly important in the formation process of the biomaterials object of the invention; particularly interesting under this profile are benzyl esters (HYAFF) with an esterification percentage preferably ranging from 5 to 50% and the hexadecyl amide of HA (HYADD4) with a derivatization degree of up to 5% (measured in HPLC), this amide has proved to be particularly relevant for its role as viscoelastic gel that can be clinically used as a synovial substitute in the case of joint injury (EP1853279).

Numerous scientific experiments have amply demonstrated how HYAFF is a completely biocompatible biodegradable polymer (Campoccia D. et al., Biomaterials, 1998, 19:2101-2127) and how the use of ester derivatives of HA for the formation of fibers (EP618817) processed in nonwoven form or as a sponge, can constitute a three-dimensional matrix that can be used in the dermatological and orthopedic fields.

ACP derivatives have been used successfully as skin fillers and as anti-adhesion gels (EP0850074), whereas for the sulfated derivative of HA, its anti-inflammatory effects are being studied as a topical component of compositions for dermatological use (EP2429515), or its protective/regenerative effect of the cartilage matrix in the case of oral or intra-articular compositions (EP2021078, EP2786782).

Consequently, the new biomaterials formed by the amide bond of the carboxyl of the above-mentioned HA derivatives with carnosine find, according to the present invention, effective use in the treatment of RA (in addition to all diseases caused directly by RA or indirectly related to/depending on RA) and OA (and also in the prevention of OA), as biomaterials processed in the form of fibers, gels, hydrogels, microspheres, sponges, woven or non-woven fabrics, films.

The diseases caused directly by RA are systemic clinical manifestations of the same pathology involving organs and apparatuses other than the joint. Specifically, there is RA in which the rheumatoid nodules have been formed at the pulmonary level with consequent pulmonary fibrosis, pleurisy and pleuropericarditis, whereas at the ocular level there is xerophthalmia, uveitis and scleritis.

The pathologies indirectly related to/depending on RA are defined herein as pathologies that have been indirectly caused by RA as they are linked to serious situations of altered immune profile and/or to conditions of high oxidative stress. An altered free radical production can in fact cause serious damage to the structure of the connective tissues, to the structure of proteins, cell membranes and DNA genes. Oxidative stress can therefore be considered as a pathological condition caused by the breaking of a delicate balance between the production and disposal of free radicals.

Oxidative stress is currently considered as actively contributing to the onset of RA and, consequently, other important diseases that frequently arise contextually and/or depend on RA, such as premature pathological aging, heart attack, stroke, arteriosclerosis and coronary atherosclerosis, arterial hypertension, dementia, diabetes, osteoporosis and amyloidosis, many forms of cancer, certain hepatic or renal diseases such as proteinuria and nephritis, gastric lesions, cataracts.

Diseases linked to an altered immune profile, on the other hand, include psoriatic arthritis, gastritis, vasculitis, type I diabetes and autoimmune diseases including, for example, autoimmune thyroiditis.

The pharmaceutical compositions comprising HA/carnosine conjugates and HA/carnosine biomaterials are described for a topical, oral, intra-articular, parenteral or surgical application, in all fields in which said administration is required in relation to the prevention or treatment of the pathologies described above and related/dependent diseases, and can be associated with pharmacologically and/or biologically active substances such as, for example, steroids, anti-inflammatory cytokines, interferon, growth factors (such as, for example, BMP2 and BMP7), NSAIDs, and/or with controlled drug delivery systems such as, for example, cyclodextrins, and/or natural polymers, such as HA and its derivatives, preferably with the amide derivative of HA with hexadecylamine called HYADD4 (EP 1095064), or of a synthetic nature.

The synthesis of the HA/carnosine conjugates object of the invention is described hereunder, whose conjugation process between carnosine methyl ester and hyaluronic acid sodium salt or tetrabutylammonium salt takes place in a medium comprising DMSO or DMSO/$H_2O$ as the main solvent.

In patent application WO2016016847 discussed above, a conjugation process between the sodium salt of HA and carnosine methyl-ester in THF was exclusively described.

In the process according to the present invention, the synthesis therefore takes place in a dipolar solvent, aprotic and strongly hygroscopic, at room temperature. The synthesis in THF according to the state of the art was effected in an aprotic, volatile solvent, having a lower polarity, and was therefore carried out at 4° C.

The chemical characteristics of the different solvents, associated with different reaction temperatures that also allow the use of a salt of HA different from the sodium salt, allowed the degrees of derivatization of HA with carnosine described and claimed hereunder, to be obtained.

Preparation Methods of the HA/Carnosine Conjugates Object of the Invention

EXAMPLE 1

Synthesis of Carnosine Methyl-Ester (as Hydrochloride Salt)

The reaction was carried out in an anhydrous environment. 1.5 g of carnosine were treated, under stirring, inside a 250 ml flask, with 50 ml of an acetyl chloride solution in anhydrous methanol (pre-mixed) in a 1:20 ratio (v/v) for 12 hours, after which about 90% of the solvent was removed by evaporation under vacuum. 20 ml of anhydrous methanol were added to the reaction residue and again about 90% of the solvent was removed by evaporation. The operation was repeated until all the HCl (which was formed during the reaction) had been removed; the product was then brought to dryness under vacuum.

The product was subjected to control by electrophoresis on paper and the various components of the sample were detected using ninhydrin.

EXAMPLE 2

Synthesis of the HA/carnosine Conjugate with DS Included Within the Range of 35±3% mol/mol)

1.1 g of hyaluronic acid sodium salt (HANa) with a MW of 700 kDa were introduced into a reactor in which 80 ml of a mixture of $H_2O$:DMSO (in a ratio of 1:1 v/v) were subsequently added under constant stirring (at room temperature) for at least 4 hours. 40 ml of a solution of $H_2O$:DMSO (1:1 v/v) containing 480 µl of Tris [2-(2-methoxyethoxy) ethyl] amine (TMEA), 4.00 mg of 3-hydroxy-1,2,3-benzotriazin-4(3H)-one (HOOBt) in powder form, and 20 ml of $H_2O$ containing 240 mg of N-(3-Dimethylaminopropyl)-N'ethylcarbodiimide hydro-chloride (EDC HCl), were then added in sequence.

After 30 minutes, 20 ml of a solution containing 365 mg of carnosine methyl ester in DMSO were added. This mixture was then subjected to vigorous stirring for 4 days at 25° C.

The product of the above reaction was then precipitated with the addition of ethanol (1L) and the deprotection (basic hydrolysis) of the methyl ester of carnosine was subsequently carried out with 0.1N NaOH, under constant stirring for 2 hours at 25° C. The pH was then neutralized by the addition of 1N HCl and the product precipitated with 800 ml of ethanol. This precipitate was then dissolved in water, dialyzed in water for 2 days and subsequently lyophilized.

EXAMPLE 3

Synthesis of the HA/Carnosine Conjugate with DS Included Within the Range of 50±5% mol/mol)

1.5 g of hyaluronic acid tetrabutylammonium salt (HATBA) with a MW of 200 kDa were introduced into a reactor in which 50 ml of DMSO were subsequently added, under constant stirring (at room temperature) for at least 4 hours. 2.4 ml of Tris [2-(2-methoxyethoxy) ethyl]amine (TMEA), 400 mg of 3-hydroxy-1,2,3-benzotriazin-4(3H)-one (HOOBt) in powder form, and 20 ml of DMSO containing 240 mg of N-(3-dimethylaminopropyl)-N'-ethylcarbodiimide hydrochloride (EDC HCl), were then added in sequence.

After 30 minutes, 10 ml of a solution containing 365 mg of carnosine methyl ester in DMSO were added. This mixture was then subjected to vigorous stirring for 1 day at 25° C.

A second addition was finally effected of 10 ml of DMSO containing 240 mg of N-(3-dimethylaminopropyl)-N'-ethylcarbodiimide hydrochloride (EDC, HCl), and 10 ml of the solution containing 365 mg of carnosine methyl-ester in DMSO.

This mixture was left under vigorous stirring for 3 days at 25° C.

The above reaction product was then precipitated with the addition of 5 ml of a saturated solution of NaBr and 800 ml of ethanol and the deprotection (basic hydrolysis) of the methyl ester of carnosine with NaOH 0.1N, was then carried out, under constant stirring for 2 hours at 25° C.

The pH was then neutralized by the addition of HCl 1N and the product precipitated with 800 ml of ethanol. This precipitate was then dissolved in water, dialyzed again in water for 2 days and subsequently lyophilized.

EXAMPLE 4

HPLC Analysis of the Sample Prepared According to Examples 2 and 3 (Quantitative Analysis of the β-alanine Present in Carnosine Bound to the Carboxyl of HA)

Preparation of the Sample the HA/carnosine conjugate was dissolved in HCl 6M at a concentration of 25 mg/ml at 70° C. for 5 minutes, then diluted $\frac{1}{10}$ in HCl 6M;
0.1 ml of the sample solution were then transferred to a test-tube to which 1.9 ml of HCl 6M were added;
the sample was hydrolyzed for 2 hours at 165° C., left to cool, and 8 ml of $H_2O$ MilliQ were then added, the whole sample was mixed until complete resuspension and filtered;
8 ml of this filtered sample were then transferred to a 20 ml flask, to which 10 ml of NaOH 1M were added;
0.2 ml of the sample thus prepared were transferred into a vial and 0.2 ml of borate buffer 0.2M, pH 9.3, and 0.2 ml of FMOC-Cl (prepared at a concentration of 1 mg/ml in ACN (acetonitrile)) were then added; reaction time: at least 30 minutes;
the sample was finally injected into HPLC using the following HPLC Method with a UV detector:
Agilent Zorbax Eclipse XDB-C18 Column (15 cm, 5µ, 100 Å)
Flow-rate: 1 ml/min
Injection volume: 50 µl
Wavelength: 262 nm
Mobile phase A: $Na_2HPO_4$ 40 mM pH 7.8
Mobile phase B: ACN/MeOH/$H_2O$ 45/45/10
Phase A/Phase B ratio=60/40 (with gradient).
Results: the sample of Example 2 showed a degree of derivatization to the carboxyl of HA of 35% mol/mol, whereas the sample of Example 3 showed a degree of derivatization equal to 50% mol/mol.

Animal Experiments of HA/Carnosine Conjugates

EXAMPLE 5

Experimental Model of RA; Collagen-Induced Arthritis (CIA) in Mice

Oral Treatment With HA/Carnosine Conjugate

CIA has for many years been recognized as a valid experimental model of RA in mice or rats, as it determines humoral, cellular, histological and pathological characteristics of RA in the animal (Holmdahl et al., Immunological reviews, 1990, 118: 193-232). Following the induction of CIA in mice, in fact, a large number of activated neutrophils/macrophages/lymphocytes are present in its joints, with the consequent production of the synovial pannus of RA.

CIA induction: Type II chicken collagen (CII) was dissolved in acetic acid 0.01M at a concentration of 2 mg/ml, the complete Freund's adjuvant (CFA) was then prepared by the addition of *Mycobacterium tuberculosis* H37Ra (2 mg/ml) to the incomplete adjuvant (composed of water/mineral oil emulsion), the two components (CII and CFA) were then mixed and emulsified in the same ratio v/v.

100 µl of the emulsion thus obtained (containing 100 µg of CII) were injected at the base of the mouse's tail by intradermal infection (day 1). A second identical injection was effected after 21 days.

Experimental Groups

Nine-week old DBA/IJ male mice were used, about 30 g each, 20 mice per group.

Group 1, CIA-control: the animals were treated by CIA induction and subsequently with distilled water administered orally every 24 hours starting from the 25th day after the CIA until the 35th day, end of the experimentation.

Group 2, CIA+HA/carnosine conjugate: the animals were treated by CIA induction and subsequently with the above-mentioned conjugate every 24 hours starting from the 25th day after the CIA until the 35th day. The conjugate used for the test had been prepared according to Example 3, it was therefore derivatized at 50% mol/mol, the dose, administered orally, was 81 mg/kg of conjugate (20 mg of carnosine and 61 mg of HA).

Group 3: CIA+HA/carnosine mixture: the animals were treated by CIA induction and subsequently with HA/carnosine every 24 hours starting from the 25th day after the CIA until the 35th day. This preparation consisted of a mixture of HA sodium salt mixed with carnosine in water, administered orally at a dose of 20 mg/kg of carnosine with 61 mg/kg of HA.

Clinical Evaluation

The development of the disease was evaluated daily 20 days after the first injection according to the following assessment scheme for each single paw:
0=no indication of the development of arthritis
1=swelling and/or redness of the paw
2=swelling and/or redness of the paw in at least 2 joints
3=swelling and/or redness of the paw in at least 3 joints
4=development of a severe form of arthritis of the entire paw with the involvement of all the fingers.

For each animal, the total CIA development index (defined as Arthritic Paw score) was calculated by summing the values obtained (and evaluated as above) for each paw.

The clinical severity index is given by the volume of the paws (measured every two days by a plethysmometer) which progressively increased throughout the whole analysis period based on the severity of the disease: foot increase.

Histological Evaluation

At the end of the evaluation period, i.e. on the 35th day after the beginning of the experimentation, the animals were sacrificed, the treated paws removed (including the knee joints) and fixed in 10% formalin subsequently decalcified and soaked in paraffin for the preparation of 5 µm microtome sections, then stained with hematoxylin/eosin. The optical microscope analysis was effected following the following Histological score:
0=no damage
1=edema
2=presence of inflammatory cell infiltrate
3=evidence of bone resorption

Plasma Analysis

Plasma Quantification of TNF-α

The TNF-α levels were measured in animal plasma at the end of the experimentation using the ELISA kit of Calbiochem-Novabiochem Corporation, IT, for determining the TNF-α levels (reading limit 10 pg/ml).

Plasma Quantification of the Lipid Peroxidation Index

The attack by free radicals of flee lipids present in the biological membranes determines the start of an oxygen-dependent deterioration process (lipid peroxidation) which leads to the impairment of the integrity of the biological membranes, and to the formation of oxidized lipid proteins and lipid peroxides, with by-products such as aldehydes including malondialdehyde (MDA). All of these processes lead to oxidative stress. In order to measure the free radical damage caused in the mouse due to the onset of CIA, plasma samples (thus containing the above aldehydes) of the groups treated taken at the end of the experimentation were reacted with barbituric acid (TBARs), in comparison with the standard given by MDA (i.e. 99% tetramethoxypropane solutions, Sigma, Milan). The result was an adduct easily detectable with a spectrophotometer OD650 nm (Ohkawa H et al., Anal. Biochem, 1979, 95: 351-358).

Results

Clinical Evaluation

As indicated in FIG. 1 (Arthritic Paw Score), the maximum index of pathological manifestation is shown with clear signs of periarticular erythema and edema of the paws 30 to 35 days after treatment with CIA (control group), oral administration of the HA/carnosine conjugate caused a significant reduction in joint inflammation, especially at 30 days, also versus the CIA group+HA/carnosine mixture. This significant difference in efficacy, index of the synergy between HA and carnosine when covalently bound to the DS experimented, is maintained for even longer times until the end of the experimentation.

Figure 2:
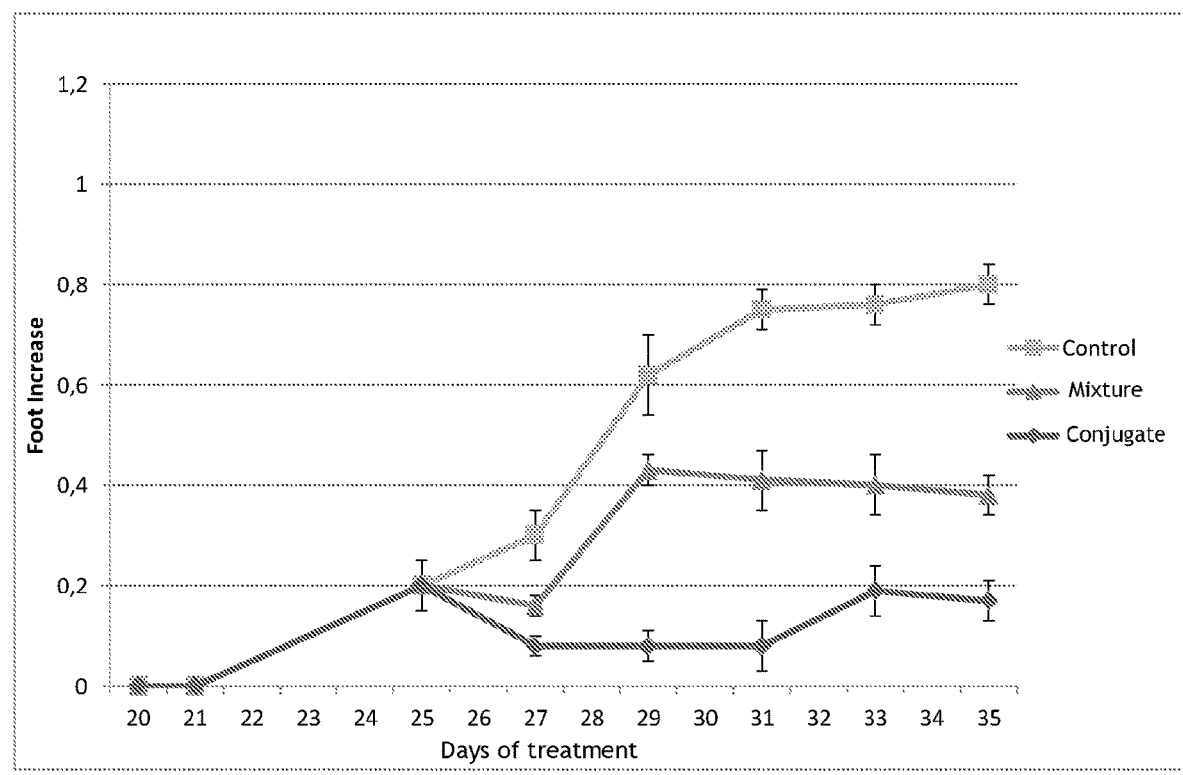
FIG. 2 shows the trend of the foot increase Example 5.

FIG. 2 shows the trend of the foot increase: also in this case the treatment with the conjugate object of the invention confirms the surprising effect of FIG. 1, in which, at the end of the experiment, the swelling of the paw treated with the conjugate was significantly lower versus both the untreated control and also versus the group being treated with the HA/Carnosine mixture.

Histological Evaluation

Figure 3:
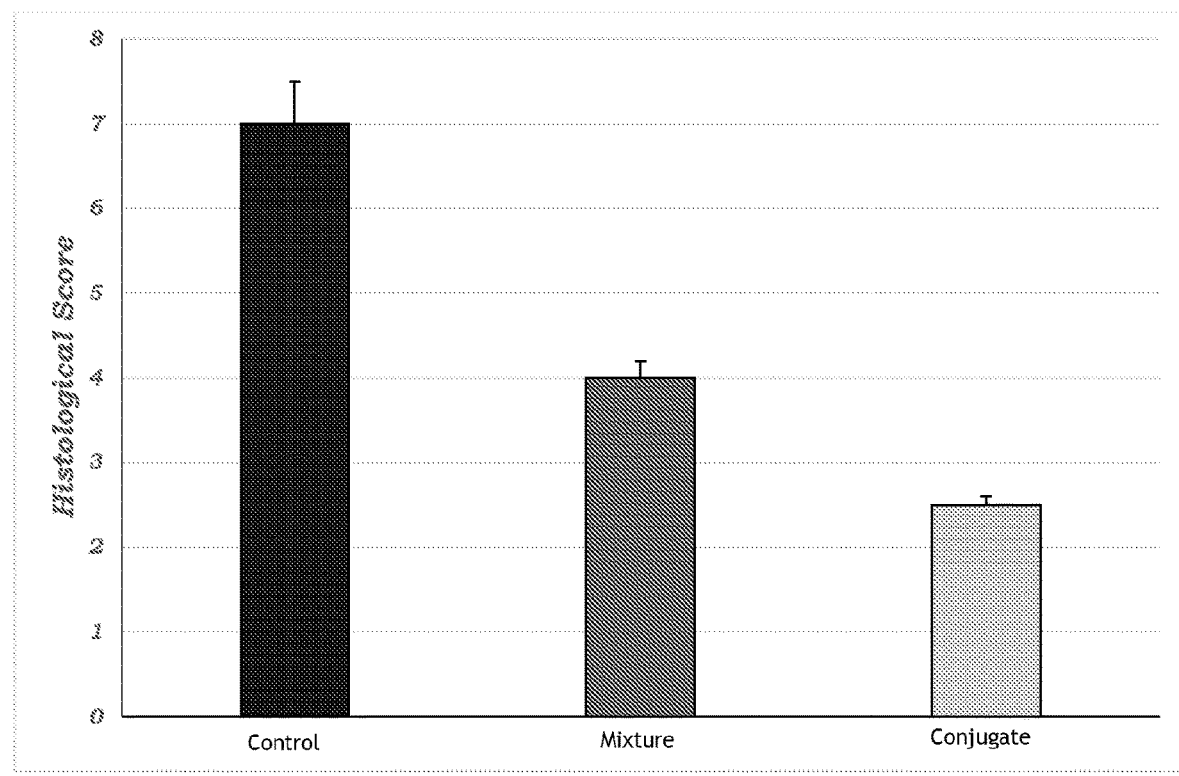
FIG. 3 shows the histological evaluation of CIA-control animals at the 35th day (end) of the experimentation.

FIG. 3: at the 35th day (end) of the experimentation, the histological evaluation of CIA-control animals revealed clear and important histological signs of the development of a severe form of RA, with bone erosion and moderate/severe necrosis of the joint tissues. Treatment with the HA/Carnosine conjugate, on the other hand, significantly reduced this erosion both versus the control and versus the group treated with the HA/Carnosine mixture.

Plasma Analysis: Plasma Quantification of TNF-α

At the end of the experimentation, the plasma level of the pro-inflammatory cytokine TNT-α was analyzed in all the animals subjected to CIA and not (Sham sample, i.e. in which CIA had not been induced to have the plasma TNF value of non-operated healthy animals as a comparison).

Figure 4:
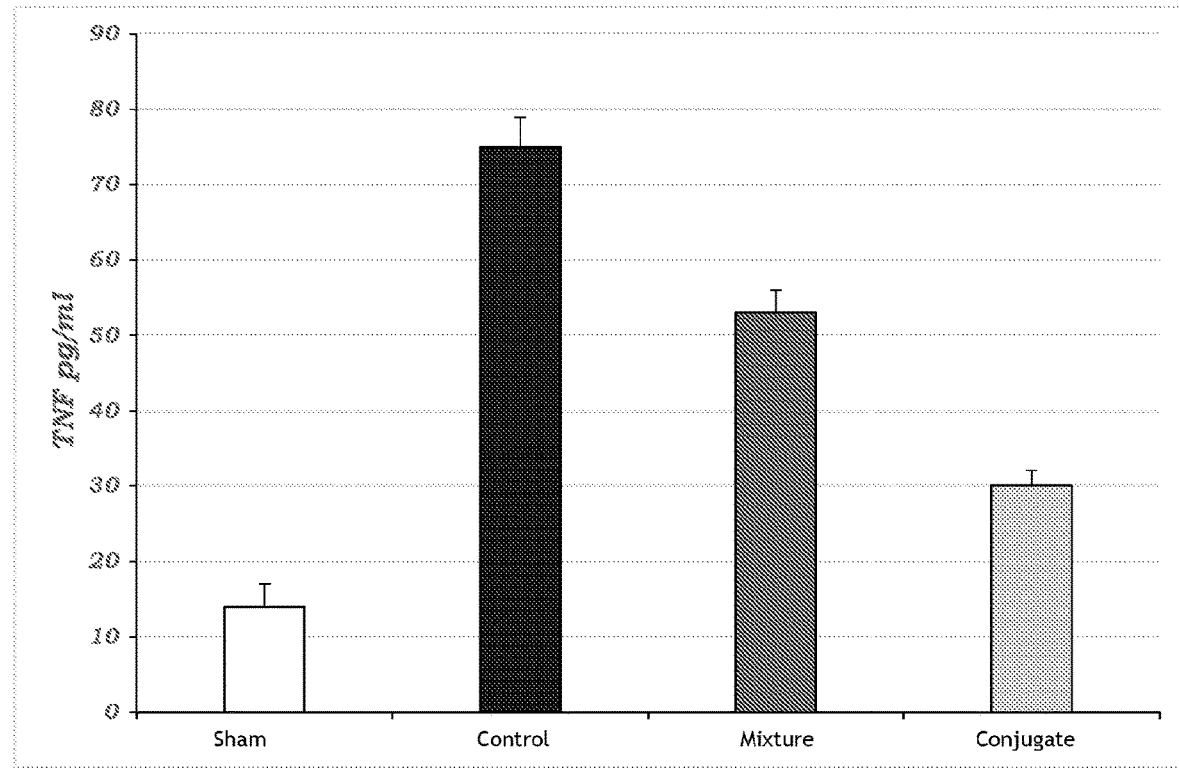
FIG. 4 shows the values of the TNF cytokine in Example 5.
Figure 5:
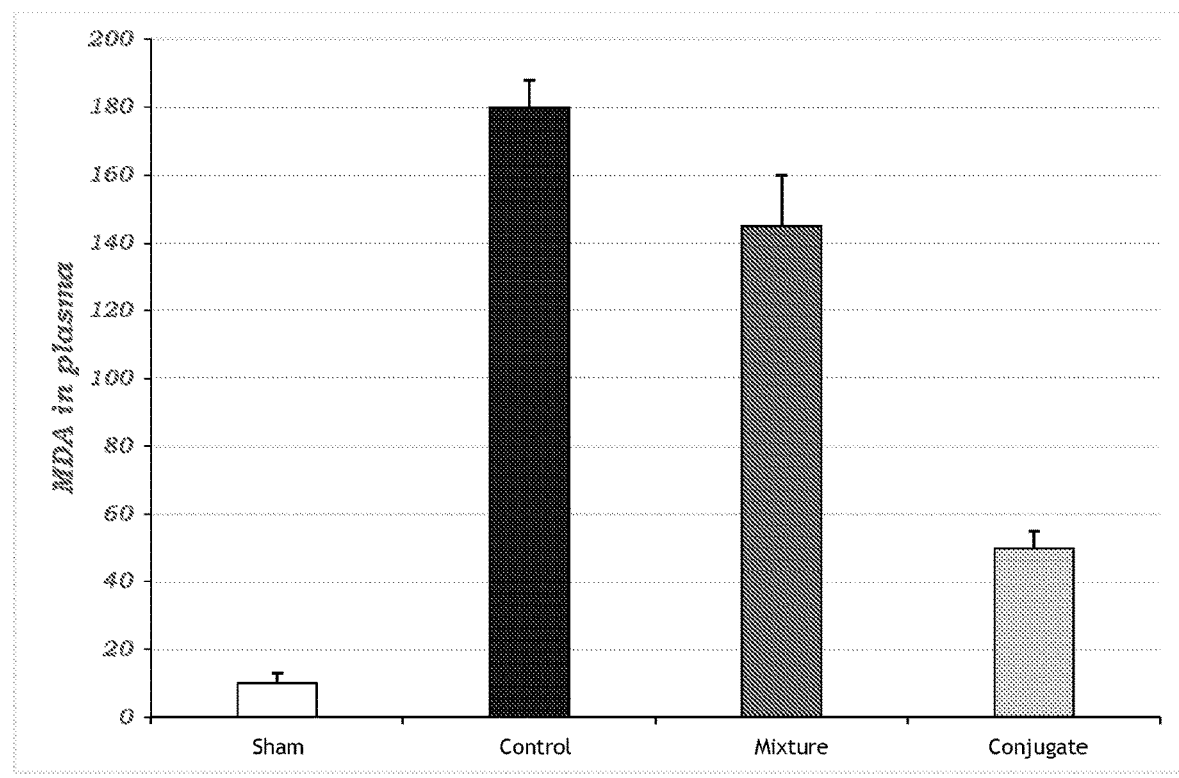
FIG. 5 shows the MDA levels in plasma in Example 5.

As shown in FIG. 4, the value of the above-mentioned inflammatory cytokine in the CIA-control group was extremely high, almost 5 times higher than the Sham control, whereas the treatment with the conjugate object of the invention more than halved the TNF-α value, also significantly reducing it versus the group to which the HA/Carnosine mixture had been administered.

EXAMPLE 6

Experimental Model of OA: Induction of Monosodium Iodoacetate (MIA) Osteoarthritis in Rats OA was induced in the posterior knee joints of the rats being tested, by the intra-articular injection of MIA: 25 µl of saline containing 1 mg/kg of MIA were injected into the joint (knee) of the right paw of each animal (under treatment) through the infrapatal ligament, whereas the left joint received an equal volume of saline 0.9% (Sagar D R et al, Ann. Rheum. Dis., 2013, 73: 1558-1565).

Intra-Articular Treatment with the HA/Carnosine Conjugate

Experimental Groups

Male Sprague-Dawley rats were used, of about 230 g each, 20 rats per group.

Group 1: MIA-control: the animals were treated by MIA induction and subsequently with 25 µl of distilled water administered intra-articularly in the right knee at day 7, 10, 13, 16 and 19 after MIA, on the 21st day, the experimentation ended with euthanasia of the animals.

Group 2: MIA+HA/carnosine conjugate: the animals were treated by MIA induction and subsequently with 25 µl of the conjugate prepared according to Example 2, then derivatized at 35% mol/mol, intra-articularly in the right knee at day 7, 10, 13, and 16 19 after MIA until the 21st day. The 25 µl of HA/carnosine conjugate contained 250 µg of conjugate, i.e. 45.75 µg of carnosine and 204.25 µg of HA.

Group 3: MIA+HA/carnosine mixture: the animals were treated by MIA induction and subsequently with 25 µl of HA and carnosine intra-articularly in the right knee at day 7, 10, 13, 16 and 19 after MIA until the 21st day. This preparation consisted of a mixture of HA sodium salt mixed with carnosine in water, therefore 25 µl of this preparation contained 45.75 µg of carnosine and 204.25 µg of HA.

Plasma Quantification of TNF-α

At the end of the experimentation, the TNF-α levels were measured in the plasma of the animals using the ELISA kit of Calbiochem-Novabiochem Corporation, IT, for determining the TNF-α levels (reading limit 10 pg/ml).

Results

Figure 6:
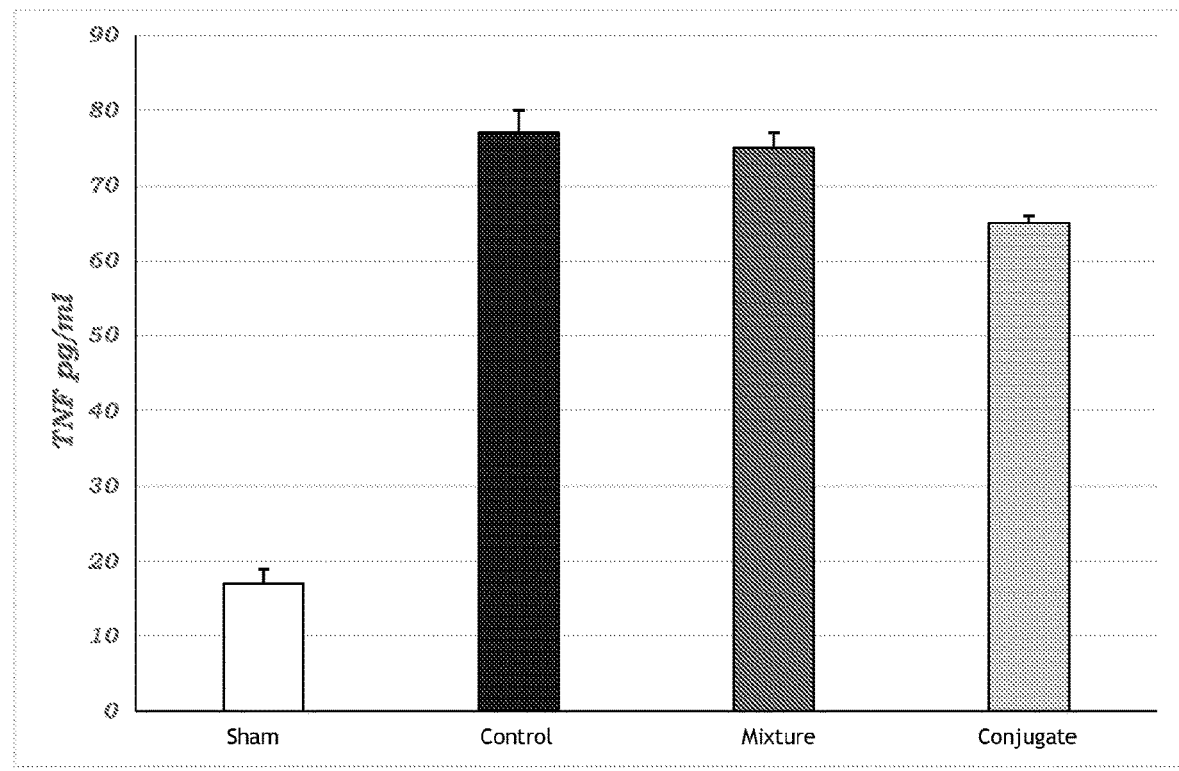
FIG. 6 shows the values of the TNF cytokine in Example 6.

FIG. 6 shows the results obtained in the treatment groups and in the Sham group, defined as a group in which the animals had not been subjected to treatment with MIA: also in this case, the plasma level of the TNF cytokine of the MIA-control group proved to be extremely high, whereas the treatment with the HA/Carnosine conjugate lowered the TNF-α value significantly not only versus this control, but also versus the group to which the HA/Carnosine mixture had been administered that did not show any efficacy, demonstrating once again the striking effect of the conjugate object of the invention, and therefore its level of derivatization which is particularly high with respect to the state of the art.

Oral Treatment with the HA/Carnosine Conjugate

Experimental Groups

Male Sprague-Dawley rats, of about 230 g each, were used, 20 rats per group.

Group 1: MIA-control: the animals were treated by MIA induction and subsequently with distilled water administered orally every 24 hours from the 3rd day after MIA until the 20th day, end of the experimentation.

Group 2: MIA+HA/carnosine conjugate: the animals were treated by MIA induction and subsequently with the above-mentioned conjugate every 24 hours from the 3rd day after MIA until the 20th day. The conjugate used for the experimentation was prepared according to Example 2, it was then derivatized at 35% mol/mol, the dose, administered orally, was equal to 88.5 mg/kg of conjugate (16.2 mg of carnosine and 72.3 mg of HA).

Group 3: MIA+HA/carnosine mixture: the animals were treated by MIA induction and subsequently with HA/carnosine every 24 hours starting from the 3rd day after MIA up to the 20th day. This preparation consisted of a mixture of HA sodium salt mixed with carnosine in water, administered orally at a dose of 16.2 mg/kg of carnosine with 72.3 mg/kg of HA.

Group 4: MIA+naproxen: the animals were treated by MIA induction and subsequently with naproxen administered orally at a dose of 10 mg/kg every 24 hours starting from the 3rd day after MIA until the 20th day.

Histological Evaluation

At the end of the experimentation period, i.e. on the 21st day from the beginning of MIA induction, the animals were sacrificed, the treated legs removed (including the knee joints) and fixed in 10% formalin. They were subsequently decalcified and soaked in paraffin for the preparation of 5 µm microtome sections, then stained with hematoxylin/eosin. The optical microscope analysis was performed following a modified Histological score by Mankin, with a score range of 0-12, i.e. from a normal cellular organization to complete disorganization and hypocellularity; (Mankin H J et al., J Bone Joint Surg Am., 1971, 53 (3): 523-537).

Results

Figure 7:
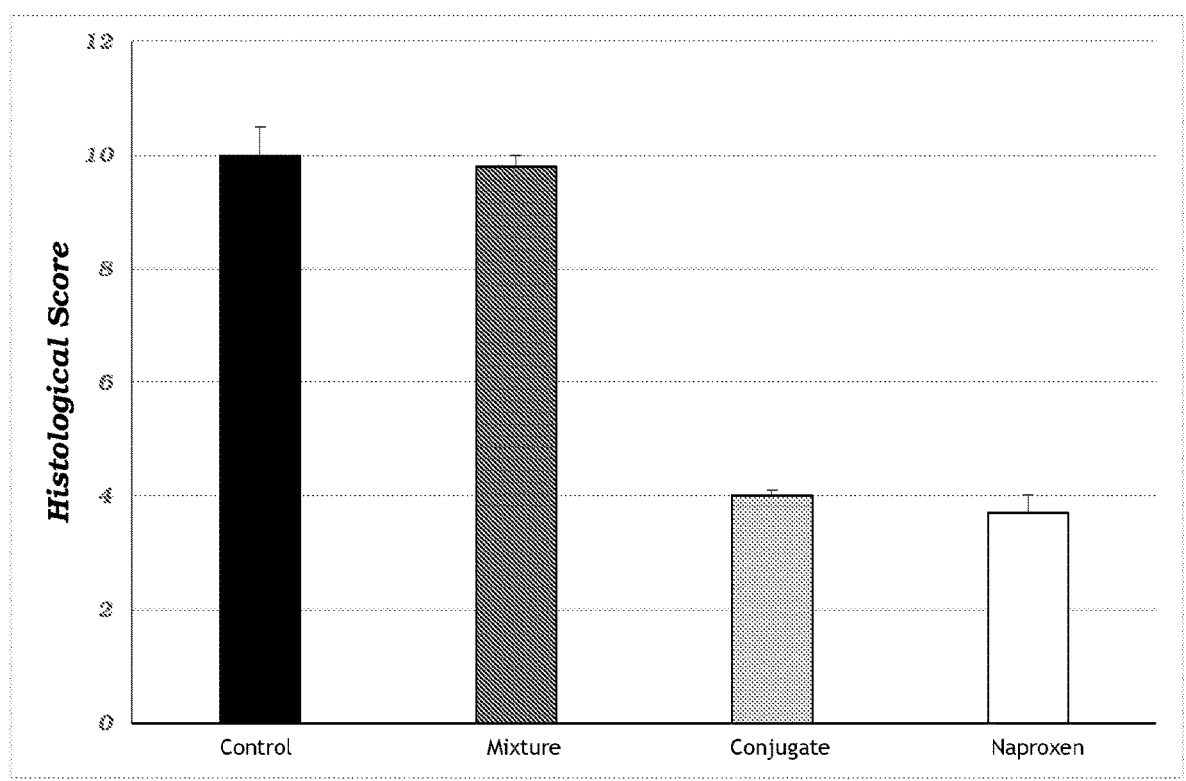
FIG. 7 shows the histological score for Example 6.

The histological examination of the samples of group 1 showed irregularities in the organization of the tissues with fibrillation of the surface layer, a reduced cellularity and degeneration of the cartilage layer. Oral treatment with the HA/carnosine conjugate very significantly reduced histological damage and cartilage degeneration, totally comparable to the effect elicited by naproxen (known NSAIDs of documented effectiveness), whereas treatment with the HA/carnosine mixture did not lead to any histological improvement with respect to the untreated samples of Group 1 (MIA-control) (FIG. 7).

The invention claimed is:

1. A method for the treatment of osteoarthritis and/or for the treatment of rheumatoid arthritis (RA), which comprises orally or intra-articularly administering an effective dose to a patient in need thereof a pharmaceutical composition comprising a hyaluronic acid (HA)/carnosine conjugate having a direct amide bond between the carboxyl group of hyaluronic acid and the amine group of carnosine, with a derivatization degree of the carboxyl group of HA ranging from 30 to 60%.

2. The method according to claim 1, which further comprises treating
   pathologies caused directly by RA selected from pulmonary fibrosis, pleurisy and pleuropericarditis, xerophthalmia, uveitis and scleritis, and/or
   pathologies indirectly related to or depending on RA selected from premature pathological aging, heart attack, stroke, arterosclerosis and coronary atherosclerosis, arterial hypertension, dementia, diabetes, osteoporosis and amyloidosis, cancer, proteinuria and nephritis, gastric lesions, cataracts, psoriatic arthritis, gastritis, vasculitis, type I diabetes and autoimmune thyroiditis.

3. The method according to claim 1, wherein the HA has an average molecular weight ranging from 400 to $3\times10^6$ Da or ranging from $1\times10^5$ Da to $1\times10^6$ Da or within the range of 130-220 k Da or within the range of 500-750 k Da and mixtures thereof.

4. The method according to claim 1, wherein the derivatization degree of HA ranges from 30 to 60% and the average molecular weight of HA ranges from $1\times10^5$ Da to $1\times10^6$, or is within the range of 130-220 k Da or 500-750 k Da and mixtures thereof.

5. The method according to claim 1, wherein the hyaluronic acid is sodium salt of HA or tetrabutylammonium salt of HA.

6. The method according to claim 1, wherein said pharmaceutical composition is administered in a form of a biomaterial comprising HA selected from esters of HA, amides of HA, internal esters of HA, percarboxylates of HA and sulfates of HA.

7. The method according to claim 6, which further comprises treating
   pathologies caused directly by RA selected from pulmonary fibrosis, pleurisy and pleuropericarditis, xerophthalmia, uveitis and scleritis, and/or pathologies indirectly related to or depending on RA selected from premature pathological aging, heart attack, stroke, arterosclerosis and coronary atherosclerosis, arterial hypertension, dementia, diabetes, osteoporosis and amyloidosis, cancer, proteinuria and nephritis, gastric lesions, cataracts, psoriatic arthritis, gastritis, vasculitis, type I diabetes and autoimmune thyroiditis.

8. The method according to claim 7, wherein the biomaterial is in the form of fibers, gels, hydrogels, microspheres, sponges, woven or nonwoven fabrics or films.

9. The method according to claim 1, wherein said pharmaceutical composition further comprises pharmacologically and/or biologically active substances and/or with controlled release systems of drugs and/or natural polymers or polymers of a synthetic nature.

10. The method according to claim 1, wherein the derivatization degree of the carboxyl group of HA varies within the range of 35±3% or 45±5%.

* * * * *